United States Patent [19]

Stanek et al.

[11] Patent Number: 5,376,685
[45] Date of Patent: * Dec. 27, 1994

[54] ARYLHYDRAZONES USING AS SAMDC INHIBITORS

[75] Inventors: Jaroslav Stanek, Arlesheim; Giorgio Caravatti, Allschwil; Jörg Frei, Hölstein; Hans-Georg Capraro, Rheinfelden, all of Switzerland

[73] Assignee: Ciba-Geigy Corporation, Ardsley, N.Y.

[*] Notice: The portion of the term of this patent subsequent to Jun. 2, 2009 has been disclaimed.

[21] Appl. No.: 58,111

[22] Filed: May 7, 1993

Related U.S. Application Data

[60] Division of Ser. No. 849,262, Mar. 11, 1992, Pat. No. 5,238,941, which is a continuation-in-part of Ser. No. 574,991, Aug. 29, 1990, Pat. No. 5,118,709, which is a division of Ser. No. 324,368, Mar. 15, 1989, Pat. No. 4,971,986.

[30] Foreign Application Priority Data

Mar. 25, 1988 [CH] Switzerland .......................... 1139/88

[51] Int. Cl.$^5$ .................... A61K 31/15; C07C 251/86
[52] U.S. Cl. .................... 514/583; 514/590; 514/634; 514/639; 514/615; 564/21; 564/36; 564/251; 564/149
[58] Field of Search .............. 564/251, 21, 36, 251, 564/149; 514/634, 583, 590, 639, 615

[56] References Cited

U.S. PATENT DOCUMENTS

| | | | |
|---|---|---|---|
| 3,174,978 | 3/1965 | Marxer | 260/319 |
| 3,206,478 | 9/1965 | Marxer | 260/343.7 |
| 3,211,746 | 10/1965 | Marxer | 260/319 |
| 3,349,099 | 10/1967 | Marxer | 260/326.14 |
| 3,560,557 | 2/1971 | Marxer | 260/501 |
| 3,673,241 | 6/1972 | Marxer | 424/319 |
| 3,753,680 | 8/1973 | Tilles | 71/120 |
| 4,076,726 | 2/1978 | Panneman et al. | 260/340.5 |
| 4,321,274 | 3/1982 | Wang et al. | 424/304 |
| 4,602,041 | 7/1986 | Newsome et al. | 514/634 |
| 4,971,986 | 11/1990 | Stanek et al. | 514/357 |

FOREIGN PATENT DOCUMENTS

| | | |
|---|---|---|
| 0087218 | 8/1983 | European Pat. Off. |
| 0377304 | 7/1990 | European Pat. Off. |
| 892205 | 11/1989 | South Africa |
| 1457911 | 12/1976 | United Kingdom |

OTHER PUBLICATIONS

Antonini, et al. "N*N*S* Tridentate Ligand System As Potential Antitumor Agents" J. Med. Chem. 24: 1181-1184 (1981).
"Hydrazones" Chem. Abs. 57: #16487c (1962).
"Amidinohydrazones of alkyl biguaridophenyl ketones" Chem. Abs. 57 #9742c (1962).
"Hydrazones" Chem. Abs. 60 #53994 (1966).
"New quanylhydrazones" Chem. Abs 60 #13191c (1964).
"New quanylhydroazones and the process for their preparation" Chem Abs. 61: #4273a (1964).
Marxer "Guanylhyrazones of biguanidinoaryl alkyl ketones" Chem. Abst. 62 #1613t (1965).

(List continued on next page.)

*Primary Examiner*—Patricia L. Morris
*Assistant Examiner*—Jacqueline Haley
*Attorney, Agent, or Firm*—Irving M. Fishman; Karen G. Kaiser

[57] ABSTRACT

Compounds of formula I

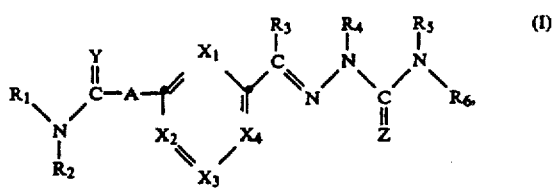

wherein A, $X_1$, $X_2$, $X_3$, $X_4$, Y, Z and $R_1$ to $R_6$ have the meanings given in the description, have valuable pharmaceutical properties and are effective especially against tumors. They are prepared in a manner known per se.

5 Claims, No Drawings

OTHER PUBLICATIONS

Marxer "Guanylhydrazones" Chem. Abs. 64 #15802c (1966).

Marxer "Guanylhydroazones" Chem. Abs. 64 #15802d (1966).

Nishimura "Guanylhydrazones" Chem. Abs. 64 #15802e (1966).

Marxer "Biguanidoaryl ketone hydroazones" Chem. Abs. 64 #19501a (1966).

Rector et al. "Anthelminitic pyridinyl acylhydrazones" Chem. Abs. 107: 77634r (1987).

Jönne, et al. "Inhibition of S-adenosylmethionine decarboxylase and diamine oxidase activities by analogues of methylglyoxal bis (guanylhydroazone) and their cellular uptake during lymphocyte activation" Bio. Chem. J. 218: 947–951 (1984).

Gan et al. "Synthesis of indanones and tetralones as new potential schistosomicidals" Chem. Abs. 105: 587 #6283c (1986).

Misra et al. "Synthesis and Antibacterial activity of Thiosemicar bazones and Hydroazones Derived from Indanone-1" J. Indian Chem. Soc. L11: 981–982 (1975).

Stegelmeier et al. "Amidinohydrazones of Tetralin chromone, thiochromone, and tetrahydroquinoline and their use in pharmaceuticals" Chem. Abs. 104: 207159v (1986).

Chikara et al. "Pyridine derivatives" Chem. Abs. 107: 77635w (1987).

Sam et al. "Potential antineoplastic agents derived from 1-2 epoxyindan" Chem. Abs 62: 6439e (1965).

Misra et al. "Synthesis and antibacterial activity of thiosemicarbazones and hydrazones derived from Indon-1-one" vol. 86: 73957m (1976).

ARYLHYDRAZONES USING AS SAMDC INHIBITORS

This is a divisional of Ser. No. 849,262, filed Mar. 11, 1992, now U.S. Pat. No. 5,238,941, which is a continuation-in-part of Ser. No. 574,991, filed Aug. 29, 1990 now U.S. Pat. No. 5,118,709 which is a divisional of Ser. No. 324,368, filed Mar. 15, 1989, now U.S. Pat. No. 4,971,986.

The invention relates to compounds of formula I

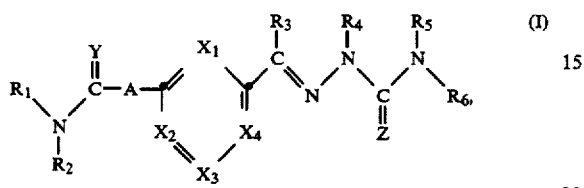

wherein A is a single bond or a group $NR_7$; each of $X_1$, $X_2$, $X_3$ and $X_4$, independently of the others, is CH or N, with the proviso that at least two of the groups $X_1$ to $X_4$ are CH; Y is $NR_8$ or also, if A is a single bond, is O; Z is $NR_9$, O or S; $R_1$ is hydrogen, lower alkyl, hydroxy, etherified or esterified hydroxy, or unsubstituted or mono- or di-substituted amino; each of the radicals $R_2$, $R_3$, $R_4$, $R_5$, $R_7$, $R_8$ and $R_9$, independently of the others, is hydrogen or lower alkyl, or $R_1$ and $R_8$ together may also be alkylene; and $R_6$ is hydrogen, lower alkyl, cycloalkyl, aryl-lower alkyl, aryl, free or functionally modified carboxy, hydroxy, etherified or esterified hydroxy, unsubstituted or mono- or di-substituted amino, tautomers thereof, and their salts, to processes for the preparation of these compounds, to pharmaceutical preparations that contain these compounds, and to the use of these compounds for the therapeutic treatment of the human or animal body or for the manufacture of pharmaceutical preparations.

Tautomers may occur, for example, when Z is $NR_9$ and $R_4$ and/or $R_5$ and/or $R_6$ is hydrogen:

The corresponding guanyl radical, shown in formula I as $-N(R_4)-C(=Z)-NR_5R_6$, may then, for example, also be the tautomeric forms $-N=C(-ZH)-NR_5R_6$, $-N(R_4)-C(-ZH)=NR_6$ or $-N(R_4)-C(-ZH)=NR_5$.

A further example:

When Y is $NR_8$ and $R_1$ and/or $R_2$ is hydrogen, then the corresponding amidine structure, shown in formula I as $-C(=Y)-NR_1R_2$, may also occur in the tautomeric forms $-C(-YH)=NR_2$ or $-C(-YH)=NR_1$. The existence of such tautomers and similar tautomers is familiar to a person skilled in the art. All of these tautomers are included in the scope of the general formula I.

Within the scope of this Application, the general definitions used hereinbefore and hereinafter have preferably the following meanings:

The prefix "lower" denotes a radical having up to and including 7, and especially up to and including 4, carbon atoms.

Lower alkyl is, for example, n-propyl, isopropyl, n-butyl, isobutyl, sec.-butyl, tert.-butyl, n-pentyl, neopentyl, n-hexyl or n-heptyl, preferably ethyl and most especially methyl.

Cycloalkyl contains, for example, from 3 to 8, preferably 5 or 6, ring carbon atoms and is, for example, cyclopropyl, cyclopentyl, cyclohexyl or cycloheptyl.

Aryl-lower alkyl is preferably phenyl-lower alkyl and especially benzyl.

Aryl is, for example, phenyl or naphthyl, such as 1- or 2-naphthyl. The phenyl or naphthyl radicals may be unsubstituted or substituted. Aryl is preferably phenyl that is unsubstituted or is substituted by lower alkyl, hydroxy, lower alkoxy, halogen, trifluoromethyl and/or by nitro, and is especially phenyl.

Free or functionally modified carboxy is preferably cyano, and also, for example, carboxy, esterified carboxy, such as, for example, lower alkoxycarbonyl, or amidated carboxy, such as, for example, carbamoyl, N-lower alkylcarbamoyl or N,N-di-lower alkylcarbamoyl.

Halogen is, for example, fluorine or iodine, especially bromine and most especially chlorine.

Etherified hydroxy is, for example, lower alkoxy. Esterified hydroxy is, for example, lower alkanoyloxy. Monosubstituted amino is, for example, lower alkylamino. Disubstituted amino is, for example, di-lower alkylamino, lower alkyleneamino, for example $C_4$–$C_7$alkyleneamino and especially $C_4$–$C_5$alkyleneamino, for example piperidino, or oxa-, thia- or aza-lower alkyleneamino, for example morpholino, thiomorpholino, piperazino or 4-lower alkylpiperazino.

The term "disubstituted amino" in the definition of the radical $R_6$ is also to be understood as meaning especially a group T

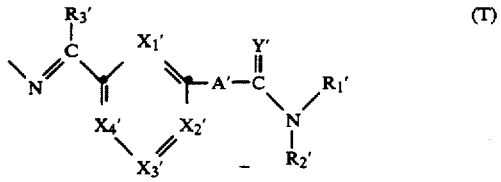

wherein A', $X'_1$, $X'_2$, $X'_3$, $X'_4$, Y', $R'_1$, $R'_2$ and $R'_3$ have the same definitions as the corresponding radicals A, $X_1$, $X_2$, $X_3$, $X_4$, Y, $R_1$, $R_2$ and $R_3$ under formula I. In a radical $R_6$ of a compound of formula I, the symbols A', $X'_1$, $X'_2$, $X'_3$, $X'_4$, Y', $R'_1$, $R'_2$ and $R'_3$ are preferably identical with the corresponding radicals A, $X_1$, $X_2$, $X_3$, $X_4$, Y, $R_1$, $R_2$ and $R_3$, so that the compounds of formula I are symmetrical with regard to their grouping $-N(R_4)-C(=Z)-N(R_5)$.

A group T is, for example, meta-amidino-(phenyl or pyridyl)-methylideneamino and especially 3-amidino-phenylmethylideneamino, 2-amidino-6-pyridylmethylideneamino, 2-amidino-4-pyridylmethylideneamino, 4-amidino-2-pyridylmethylideneamino or 4-amidino-2-pyrimidylmethylideneamino.

Alkylene formed by the radicals $R_1$ and $R_8$ together is especially $-(CH_2)_2$ or $-(CH_2)_3-$ and most especially $-(CH_2)_2-$. In the latter case, the group $-C(=NR_8)-NR_1R_2$ ($R_2$=H) corresponds to a 4,5-dihydroimidazol-2-yl radical ($\neq$ 2-imidazolinyl).

Salts of compounds according to the invention are especially pharmaceutically acceptable non-toxic salts. For example, compounds of formula I having basic groups may form acid addition salts, for example with inorganic acids, such as hydrochloric acid, sulfuric acid or phosphoric acid, or with suitable organic carboxylic or sulfonic acids, for example acetic acid, fumaric acid or methanesulfonic acid, or, for example, with amino acids, such as arginine or lysine. When several basic groups are present, mono- or poly-salts may be formed. Compounds of formula I having an acid group, for example carboxy, and a basic group, for example amino, may also be, for example, in the form of internal salts, i.e. in zwitterionic form, or part of the molecule may be in the form of an internal salt and another part may be in the form of a normal salt.

For isolation or purification it is also possible to use pharmaceutically unsuitable salts, for example picrates or perchlorates. Only the pharmaceutically acceptable non-toxic salts are used therapeutically and these are therefore preferred.

Depending on the structural conditions, the compounds of this invention may be in the form of mixtures of isomers or in the form of pure isomers.

The compounds according to the invention have valuable, especially pharmacologically useful, properties. In particular, they have a strong, specific inhibiting action on the enzyme S-adenosylmethionine decarboxylase (SAMDC). SAMDC, as a key enzyme, plays an important role in polyamine synthesis which occurs in virtually all cells of mammals, including humans. SAMDC regulates the polyamine concentration in the cell. Inhibition of the enzyme SAMDC results in a reduction in the polyamine concentration. Since a reduction in the polyamine concentration causes inhibition of cell growth, it is possible by administering SAMDC-inhibiting substances to inhibit the growth of both eucaryotic and procaryotic cells and even to kill cells or inhibit the commencement of cell differentiation.

Inhibition of the enzyme SAMDC can be demonstrated, for example, with the method of H. G. Williams-Ashmann and A. Schenone, Biochem. Biophys. Res. Communs. 46, 288 (1972). The compounds of the invention have $IC_{50}$ values of at least 0.05 μM approximately.

A further advantage of the compounds according to the invention is that they inhibit diaminoxidase only to a small extent in comparison with their strong inhibiting action on SAMDC and are well tolerated. According to J. Jaenne and D. R. Morris, Biochem. J. 218, 974 (1984), the inhibition of diaminoxidase is disadvantageous, since it can lead to the accumulation of putrescine and an indirect activation of SAMDC.

The compounds of formula I are therefore useful, for example, for the treatment of benign and malignant tumours. They are able to bring about tumour regression and also to prevent the spread of tumour cells and the growth of micrometastases. Furthermore, they can be used, for example, for the treatment of protozoa infections, such as, for example, trypanosomiasis, malaria or inflammation of the lungs caused by *Pneumocystis carinii*.

As selective SAMDC inhibitors, the compounds of formula I can be used on their own or in combination with other pharmacologically active substances. Possible combinations are, for example, those with (a) inhibitors of other enzymes of polyamine biosynthesis, e.g. ornithine decarboxylase inhibitors, (b) inhibitors of protein kinase C, (c) inhibitors of tyrosine protein kinase, (d) cytokines, (e) negative growth-regulators, (f) aromatase inhibitors, (g) anti-oestrogens or (h) classical cytostatically active substances.

Preferred compounds of formula I are those wherein A is a single bond or a group $NR_7$; each of $X_1$, $X_2$, $X_3$ and $X_4$, independently of the others, is CH or N, with the proviso that at least two of the groups $X_1$ to $X_4$ are CH; Y is $NR_8$ or also, if A is a single bond, is O; Z is $NR_9$, O or S; $R_1$ is hydrogen, lower alkyl, hydroxy, lower alkoxy or amino; each of the radicals $R_2$, $R_3$, $R_4$, $R_5$, $R_7$, $R_8$ and $R_9$, independently of the others, is hydrogen or lower alkyl, or $R_1$ and $R_8$ together may also be —$(CH_2)_2$— or —$(CH_2)_3$—; and $R_6$ is hydrogen, lower alkyl, hydroxy, amino or a group

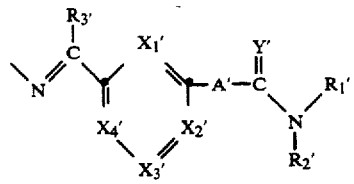

wherein A', $X'_1$, $X'_2$, $X'_3$, $X'_4$, Y', $R'_1$, $R'_2$ and $R'_3$ have the same definitions as the corresponding radicals A, $X_1$, $X_2$, $X_3$, $X_4$, Y, $R_1$, $R_2$ and $R_3$, tautomers thereof, and their salts.

Especially preferred compounds of formula I are those wherein A is a single bond or an NH group; the radicals $X_1$, $X_2$, $X_3$ and $X_4$ have the following meanings:
$X_1 = X_2 = X_3 = X_4 = CH$
$X_1 = N$, $X_2 = X_3 = X_4 = CH$
$X_2 = N$, $X_1 = X_3 = X_4 = CH$
$X_3 = N$, $X_1 = X_2 = X_4 = CH$
$X_4 = N$, $X_1 = X_2 = X_3 = CH$
$X_1 = X_2 = N$, $X_3 = X_4 = CH$
$X_1 = X_3 = N$, $X_2 = X_4 = CH$
$X_1 = X_4 = N$, $X_2 = X_3 = CH$;
Y is $NR_8$ or also, if A is a single bond, is O; Z is $NR_9$, O or S; $R_1$ is hydrogen, lower alkyl, hydroxy, lower alkoxy or amino; each of the radicals $R_2$, $R_3$, $R_8$ and $R_9$, independently of the others, is hydrogen or lower alkyl, or $R_1$ and $R_8$ together may also be —$(CH_2)_2$—; $R_4$ and $R_5$ are hydrogen, and $R_6$ is hydrogen, lower alkyl, hydroxy, amino, 3-amidinophenylmethylideneamino or 2-amidino-6-pyridylmethylideneamino, tautomers thereof, and their salts.

More especially preferred compounds of formula I are those wherein A is a single bond or an NH group; wherein (a) $X_1$, $X_2$, $X_3$ and $X_4$ are CH, or (b) $X_1$ is N and $X_2$, $X_3$ and $X_4$ are CH, or (c) $X_2$ is N and $X_1$, $X_3$ and $X_4$ are CH, or (d) $X_1$ and $X_4$ are N and $X_2$ and $X_3$ are CH; Y is $NR_8$ or also, if A is a single bond, is O; Z is NH or S; $R_1$ is hydrogen, lower alkyl, hydroxy, lower alkoxy or amino; each of the radicals $R_2$, $R_3$ and $R_8$, independently of the others, is hydrogen or lower alkyl, or $R_1$ and $R_8$ together may also be —$(CH_2)_2$—; $R_4$ and $R_5$ are hydrogen, and $R_6$ is hydrogen, lower alkyl, hydroxy, amino, 3-amidinophenylmethylideneamino or 2-amidino-6-pyridylmethylideneamino, tautomers thereof, and their salts.

Most especially preferred compounds of formula I are those wherein A is a single bond or an NH group; wherein (a) $X_1$, $X_2$, $X_3$ and $X_4$ are CH, or (b) $X_1$ is N and $X_2$, $X_3$ and $X_4$ are CH, or (c) $X_2$ is N and $X_1$, $X_3$ and $X_4$ are CH, or (d) $X_1$ and $X_4$ are N and $X_2$ and $X_3$ are CH; Y is NH or also, if A is a single bond, is O; Z is NH or S; $R_1$ is hydrogen, lower alkyl, hydroxy, lower alkoxy or amino; $R_3$ is hydrogen or lower alkyl; $R_2$, $R_4$ and $R_5$ are hydrogen, and $R_6$ is hydrogen, lower alkyl, hydroxy or amino, tautomers thereof, and their salts.

Also preferred are compounds of formula I wherein A is a single bond or a group $NR_7$; each of $X_1$, $X_2$, $X_3$ and $X_4$, independently of the others, is CH or N, with the proviso that at least two of the groups $X_1$ to $X_4$ are CH; Y is $NR_8$ or also, if A is a single bond, is O; Z is $NR_9$, O or S; each of the radicals $R_1$, $R_2$, $R_3$, $R_4$, $R_5$, $R_7$, $R_8$ and $R_9$, independently of the others, is hydrogen or lower alkyl, and $R_6$ is hydrogen, lower alkyl, hydroxy, amino or 3-amidinophenylmethylideneamino, tautomers thereof, and their salts.

Also especially preferred are compounds of formula I wherein A is a single bond or an NH group; the radicals $X_1$, $X_2$, $X_3$ and $X_4$ have the following meanings:

$X_1=X_2=X_3=X_4=CH$
$X_1=N, X_2=X_3=X_4=CH$
$X_2=N, X_1=X_3=X_4=CH$
$X_3=N, X_1=X_2=X_4=CH$
$X_1=X_2=N, X_3=X_4=CH$
$X_1=X_3=N, X_2=X_4=CH$
$X_1=X_4=N, X_2=X_3=CH$;

Y is $NR_8$ or also, if A is a single bond, is O; Z is $NR_9$, O or S; each of the radicals $R_1$, $R_2$, $R_3$, $R_8$ and $R_9$, independently of the others, is hydrogen or lower alkyl, $R_4$ and $R_5$ are hydrogen, and $R_6$ is hydrogen, lower alkyl, hydroxy, amino or 3-amidinophenylmethylideneamino, tautomers thereof, and their salts.

Preferred compounds of formula I are furthermore those wherein A is a single bond or an NH group, each of $X_1$ and $X_2$, independently of the other, is CH or N, with the proviso that at least one of the groups $X_1$ and $X_2$ is CH; $X_3$ and $X_4$ are CH; Y is NH or also, if A is a single bond, is O; Z is NH or S; the radical $R_3$ is hydrogen or lower alkyl; $R_1$, $R_2$, $R_4$ and $R_5$ are hydrogen, and $R_6$ is hydrogen, lower alkyl, hydroxy or amino, tautomers thereof, and their salts.

As sub-groups of a group of compounds of formula I, prominence is to be given to each of the following:

(a) compounds of formula I wherein A is a single bond, (b) compounds of formula I wherein A is a single bond and Y is NH, (c) compounds of formula I wherein Z is NH and $R_5$ and $R_6$ are hydrogen, (d) compounds of formula I wherein $X_1$ is N and $X_2$, $X_3$ and $X_4$ are CH, (e) compounds of formula I wherein $X_1$, $X_2$, $X_3$ and $X_4$ are CH, (f) compounds of formula I wherein $X_1$ and $X_4$ are N and $X_2$ and $X_3$ are CH, and (g) compounds of formula I wherein $X_1$ and $X_2$ are N and $X_3$ and $X_4$ are CH.

The invention relates most especially to the specific compounds described in the Examples and salts thereof.

The compounds of formula I can be prepared in a manner known per se by, for example, a) condensing a compound of formula II

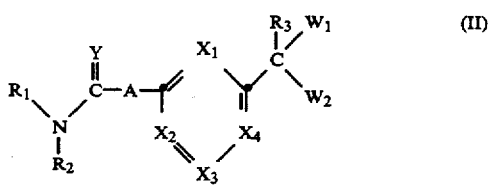

wherein the group $CW_1W_2$ is carbonyl, functionally modified carbonyl or protected carbonyl, with an amine of formula III

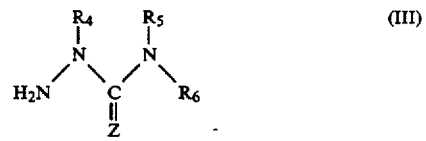

or b) for the preparation of a compound of formula I wherein A is a group $-NR_7-$, reacting a compound of formula IV

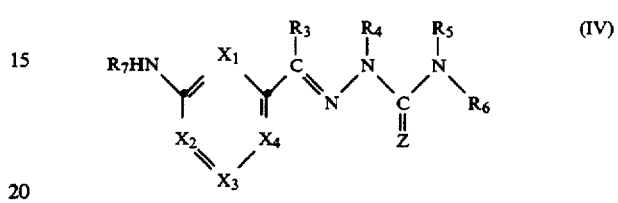

with a reagent suitable for converting the group $-NH-R_7-$ into a guanidine of formula I, or c) for the preparation of a compound of formula I wherein A is a single bond, in a compound of formula VI

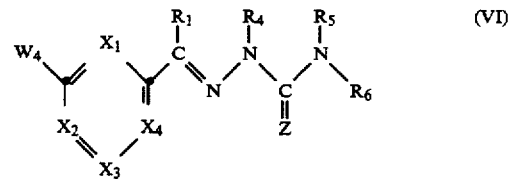

wherein $W_4$ is a radical that can be converted into an amidine or a carbamoyl compound of formula I, converting the radical $W_4$ into the group $-C(=Y)NR_1R_2$; the symbols A, $X_1$, $X_2$, $X_3$, $X_4$, Y, Z and $R_1$ to $R_7$ in the above starting materials of formulae II to VI being as defined for formula I; and, if desired, converting a resulting compound of formula I into another compound of formula I, and/or, if desired, converting a resulting salt into the free compound or into another salt, and/or, if desired, converting a resulting free compound of formula I having salt-forming properties into a salt.

In the detailed description of Processes a) to c) which follows, the symbols A, $X_1$, $X_2$, $X_3$, $X_4$, Y, Z and $R_1$ to $R_9$ are as respectively defined for formula I, unless stated otherwise.

Process a):

Examples of functionally modified or protected carbonyl $CW_1W_2$ are: di-lower alkoxymethyl, $C_1-C_2$alkylenedioxymethyl, dihalomethyl, di-lower alkylthiomethyl or $C_1-C_2$alkylenedithiomethyl.

The condensation reaction in accordance with Process a) is carried out under the conditions that known per se for the formation of hydrazones. It is preferably catalysed by an acid. In compounds of formula II, suitable protected carbonyl groups $CW_1W_2$ are those that are converted into free carbonyl under the conditions of the condensation reaction.

In order to prepare compounds of formula I wherein $R_6$ is amino, it is advisable to use the compound of formula III in excess. If stoichiometric quantities of the compound of formula III are used, then a mixture consisting of a compound of formula I wherein $R_6$ is amino and another compound of formula I wherein $R_6$ corresponds to a radical T as defined above is normally obtained. Exclusively the latter compound of formula I is obtained if 1 equivalent of a compound of formula II is reacted with 0.5 equivalent of a compound of formula III.

The intermediates of formula II wherein A is a single bond and Y is NH are obtained, for example, by treating a compound of formula VII

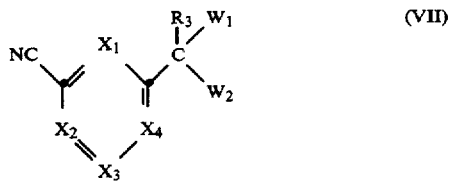

(VII)

wherein the group $CW_1W_2$ is as defined for formula II, for example with ethanol and hydrochloric acid in, for example, chloroform or diethyl ether, which results in the formation of the corresponding iminoethyl ester hydrochloride which can be converted into the desired carboximidamide of formula II, for example by reaction with ammonia or a primary or secondary amine of formula $NHR_1R_2$ and, for example, methanol.

Another possible method of preparing compounds of formula II comprises first converting a compound of formula VII by treatment with hydrogen sulfide into the corresponding thionocarboxamide [—C(=S)—$NH_2$]. The latter can also be obtained by another method, starting from the analogous carboxamide [—C(=O)—$NH_2$], for example by reaction with Lawesson reagent [2,4-bis-(4-methoxyphenyl)-2,4-dithioxo-1,3,2,4-dithiadiphosphetane]. The thionocarboxamides are S-alkylated, for example with lower alkyl iodides, and thus converted into imino-lower alkyl thiol ester hydroiodides [—C(=NH)—S-alkyl . HI] which can readily be converted by reaction with ammonia or amines of formula $NHR_1R_2$ into the desired carboximidamides of formula II [see S. Patai (Ed.), The Chemistry of amidines and imidates, Wiley, London etc. 1975, pp. 303–304].

Intermediates of formula II wherein A is the group —$NR_7$— and Y is $NR_8$ are known per se or are prepared, for example, by reacting a compound of formula VIII

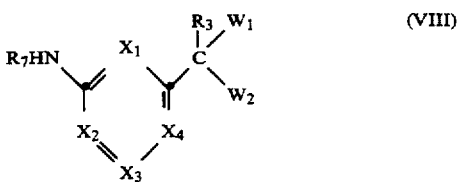

(VIII)

wherein the group $CW_1W_2$ is as defined for formula II, with an S-alkyl-isothiuronium salt of formula IX

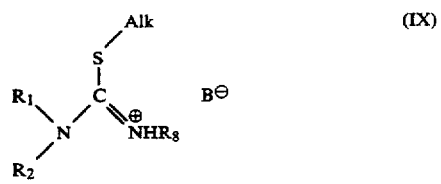

(IX)

wherein Alk is lower alkyl and $B^\ominus$ is an anion, to give the desired guanyl compound of formula II.

The preparation of compounds of formula VII is known per se [see, for example, J. Org. Chem. 44, 2702 (1979)]. Compounds of formula VII wherein $R_3$ is hydrogen and (a) $X_4=N$, $X_1=X_2=X_3=CH$,
(b) $X_1=X_2=N$, $X_3=X_4=CH$,
(c) $X_1=X_4=N$, $X_2=X_3=CH$,
(d) $X_2=X_4=N$, $X_1=X_3=CH$,
(e) $X_1=X_3=N$, $X_2=X_4=CH$,
(f) $X_2=X_3=N$, $X_1=X_4=CH$ or
(g) $X_3=X_4=N$, $X_1=X_2=CH$ can be obtained, for example, from the corresponding cyanomethyl compounds of formula X

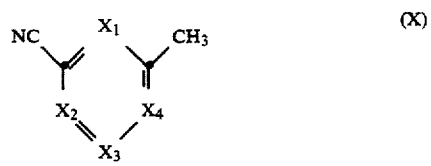

(X)

by oxidation, for example by the King-Kröhnke method in which the methyl compound of formula X which is to be oxidised is reacted first with $I_2$/pyridine and then with p-nitroso-N,N-dimethylaniline and finally is hydrolysed with hydrochloric acid (see, for example, Houben-Weyl, Vol. E3, Thieme Verlag Stuttgart, New York 1983, p. 232).

The preparation of compounds of formula X is known per se. A compound of formula X wherein $X_2=X_3=N$ and $X_1=X_4=CH$ can be obtained, for example, from 5-methylpyridazin-3-one by reaction with $PCl_5$ or $POCl_3$ and by reaction of the resulting 3-chloro compound with, for example, copper(I) cyanide in dimethylformamide at elevated temperature. A compound of formula X wherein $X_3=X_4=N$ and $X_1=X_2=CH$ can be obtained in a completely analogous manner, for example from 6-methylpyridazin-4-one by reaction with $PCl_5$ or $POCl_3$ and by reaction of the resulting 4-chloro compound with Cu(I)CN in DMF.

Compounds of formula VII, especially those wherein $X_1$ and $X_4$ are N and $X_2$ and $X_3$ are CH, can also be prepared, for example, as follows: starting from 6-hydroxy-2,4-dimethylpyrimidine, (a) by selective condensation of the 2-methyl group with benzaldehyde, (b) conversion of the 6-hydroxy group into 6-chloro by means of a chlorinating agent, e.g. $POCl_3$, and (c) selective removal of the 6-chloro substituent by reduction, e.g. with $H_2$/Lindlar catalyst (5% Pd on $CaCO_3$, contaminated with Pb), 4-methyl-2-(2-phenylethenyl)-pyrimidine is obtained. In the latter, the 4-methyl group (d) is converted, e.g. by treatment with metallic sodium and n-butyl nitrite, into 4-(N-hydroxyiminomethyl) (oxime) and the latter (e) is converted, e.g. by treatment with $POCl_3$, into a 4-cyano group. (f) Ozonolysis of the resulting 4-cyano-2-(2-phenylethenyl)-pyrimidine finally results in the desired compound of formula VII.

Compounds of formula VII wherein $R_3$ is lower alkyl can be prepared in a manner known per se from corresponding compounds of formula VII wherein $R_3$ is hydrogen. This is accomplished (a) by reaction with cyclohexylamine, treatment of the resulting azomethine with sodium hydride and a di-lower alkyl sulfoxide and, finally, acid hydrolysis [see Can. J. Chem. 48, 570 (1970)], (b) by converting the aldehyde ($R_3=H$) into the corresponding 1,2-ethylene- acetal or 1,3-propylene-acetal and reaction thereof with lower alkyllithium [see J. Org. Chem. 30, 226 (1965)] or (c) by reaction with diazo-lower alkane, each of these methods being carried out, if necessary, after previously protecting the cyano function in the molecule with a cyano-protecting group that is known per se and with the subsequent removal thereof.

The preparation of compounds of formula VIII is known per se. For example, compounds of formula VIII, and preferably those wherein $X_1$ and/or $X_2$ are N, can be obtained, for example, by reacting a corresponding halogen compound of formula XI

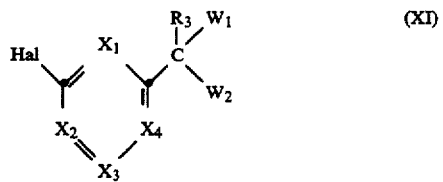

wherein Hal is halogen and the group $CW_1W_2$ is as defined for formula II, with ammonia or an amine of formula $R_7NH_2$.

Compounds of formula VIII wherein $R_7$ is hydrogen can also be obtained, for example, from corresponding compounds of formula VII by first hydrolysing the cyano group to carboxy and then carrying out, for example, a Curtius degradation, i.e. converting the carboxy group into the corresponding azide and thermally decomposing the latter. This reaction is accomplished especially easily if a modified Curtius reaction, using $(C_6H_5O)_2P(=O)-N_3$, is carried out [see Tetrahedron 30, 2151–57 (1974)].

A further possible method of preparing compounds of formula VIII wherein $R_7$ is hydrogen comprises reducing corresponding nitro compounds.

Compounds of formula VIII wherein $R_7$ is lower alkyl can be prepared, for example, from corresponding compounds of formula VIII wherein $R_7$ is hydrogen by alkylation with alkylating agents, for example lower alkyl iodides or bromides.

The preparation of aminoguanidines, aminoureas and aminothioureas of formula III is known per se. Amino(-thio)ureas [$\neq$ semi(thio)carbazides] are prepared, for example, in a manner analogous to that of corresponding (thio)ureas. For example, instead of amines, the corresponding hydrazines of formula $H_2N-NHR_4$ are used and are reacted, for example, with an isocyanate of formula $R_5N=C=O$ or $R_6N=C=O$, an isothiocyanate of formula $R_5N=C=S$ or $R_6N=C=S$, a carbamoyl chloride of formula $R_5R_6N-COCl$ or a thionocarbamoyl chloride of formula $R_5R_6N-CSCl$. The reaction of a hydrazine of formula $H_2N-NHR_4$ with an acyl isothiocyanate, for example acetyl isothiocyanate, and subsequent acid hydrolysis is, for example, also possible.

Aminoguanidines of formula III wherein Z is $NR_8$ and $R_4$, $R_5$, $R_6$ and $R_8$ are as defined for formula I are known per se and can be prepared, for example, from corresponding aminothioureas of formula III by converting the latter by alkylation, for example with an alkyl p-toluenesulfonate or alkyl halide, into the corresponding S-alkylisothiuronium salts and reacting those salts with an amine of formula $NHR_5R_6$.

Process b):

As reagents capable of converting the group $-NHR_7$ in a compound of formula IV into a guanidine of formula I there are suitable, for example, compounds of formula V

wherein $W_3$ is functionally modified carboxy.

In the preparation of guanidines of formula I ($Y \neq NR_7$), the group $W_3$ in a compound of formula V may be, for example: cyano or $-C(=^{\oplus}NHR_7)$—S-lower alkyl $B^{\ominus}$. The formation of guanidines of formula I in the reaction of amines of formula IV with unsubstituted or mono- or di-substituted cyanamides of formula V ($W_3 \neq CN$) or with unsubstituted or mono- or di-substituted S-alkylthiuronium salts of formula V ($W_3 \neq -C(=^{\oplus}NHR_7)$—S-lower alkyl $B^{\ominus}$) is known per se.

The intermediates of formula IV are prepared, for example, by condensing a compound of formula VIII wherein the group $CW_1W_2$ is as defined for formula II with an amine of formula III. The reaction that takes place corresponds to Process a) described above. If necessary, prior to the reaction, the amino group $NHR_7$ in the intermediate of formula IV should be protected by one of the $NH_2$-protecting groups conventionally employed in organic chemistry. When condensation is complete, the protecting group can be split off in a manner known per se, and an intermediate of formula IV is obtained.

Process c):

In the intermediates of formula VI, $W_4$ is, for example, free or functionally modified carboxy, especially halocarbonyl, cyano, imino-lower alkoxycarbonyl or imino-lower alkylthiolcarbonyl.

In the preparation of amidines of formula I ($Y \neq NR_7$), the group $W_4$ in a compound of formula VI may be, for example: an acid addition salt of an imino-lower alkyl ester ($\neq$imino-lower alkyl ether) or imino-lower alkyl thiol ester, for example $-C(=NH)-OC_2H_5 \cdot HCl$ or $-C(=NH)-SC_2H_5 \cdot HI$, respectively, or cyano.

Reaction of an imino-lower alkyl ester of formula VI (in the form of a salt) with ammonia or primary or secondary amines gives the unsubstituted or mono- or disubstituted amidines of formula I. A cyano compound of formula VI can be converted into an unsubstituted or mono- or di-substituted amidine of formula I, for example, by reaction with an alkali metal amide, e.g. $KNH_2$, or by reaction with a primary or secondary (di-)lower alkylammonium halide, e.g. $^{\oplus}NH_3CH_3Cl^{\ominus}$.

If an imino-lower alkyl ester of formula VI is reacted with an $\alpha,\omega$-diaminoalkane, e.g. 1,2-diaminoethane or 1,3-diaminopropane, then a compound of formula I wherein the radicals $R_1$ and $R_8$ together are alkylene is obtained.

In the preparation of carbamoyl compounds of formula I ($Y \neq O$), the group $W_4$ in a compound of formula VI may be, for example: carboxy, halocarbonyl (e.g.

—COCl), lower alkoxycarbonyl or cyano. The formation of unsubstituted or mono-or di-substituted carbamoyl compounds of formula I from corresponding intermediates of formula VI wherein $W_4$ is carboxy, halocarbonyl or lower alkoxycarbonyl, by reaction with ammonia or primary or secondary amines is known per se. Intermediates of formula VI wherein $W_4$ is cyano may be converted into unsubstituted or mono- or di-substituted carbamoyl compounds of formula I, for example, by partial hydrolysis, in the manner of a Graf-Ritter reaction, or by way of carboxylic acid ester imide salts. The conditions in the hydrolysis of cyano intermediates can be so selected that the reaction is terminated at the stage of the amide. Especially advantageous for this purpose is hydrolysis with acids, there being suitable, for example, 80% sulfuric acid (with heating), polyphosphoric acid (at 110°–150° C.), hydrogen bromide/glacial acetic acid (room temperature, formic acid or without solvent), HCl gas in ethereal solution followed by the addition of water or aqueous hydrochloric acid, or boron halides.

By means of the Graf-Ritter reaction, it is also possible to prepare N-substituted amides from nitriles of formula VI. For this, the nitriles are reacted in the presence of a strong acid, especially 85–90% sulfuric acid, or alternatively polyphosphoric acid, formic acid, boron trifluoride or other Lewis acids, but not aluminium chloride, with compounds that are able to form carbenium ions in the acid medium, that is to say, for example, with olefins, such as propylene, or alcohols, such as ethanol.

The carboxylic acid ester imides are obtained, for example, by acid-catalysed addition of alcohols to the nitriles of formula VI. The amides are obtained from the ester imides in the manner of a Pinner cleavage by thermal decomposition of the ester imide salts at temperatures above approximately 80° C.

Compounds of formula VI wherein $W_4$ is cyano can be prepared, for example, by reacting a compound of formula VII with a compound of formula III in accordance with Process a). From compounds of formula VI wherein $W_4$ is cyano, it is possible, in a manner known per se or as described above, to prepare the other compounds of formula VI, wherein $W_4$ is free carboxy or carboxy functionally modified in a form other than cyano.

Compounds of formula I can be converted into other compounds of formula I.

For example, upon reacting a compound of formula I wherein $R_6$ is amino with a compound of formula II there is obtained a compound of formula I wherein $R_6$ is a radical T as defined hereinbefore. In this manner, it is also possible to prepare corresponding compounds of formula I that are asymmetrical with regard to their grouping

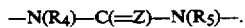

Free compounds of formula I having salt-forming properties that are obtainable by the process of the invention can be converted into their salts in a manner known per se: compounds having basic properties, for example, by treatment with acids or suitable derivatives thereof, and compounds having acid properties, for example, by treatment with bases or suitable derivatives thereof.

Owing to the close relationship between the compounds of formula I in free form and in the form of salts, throughout this specification there is to be understood by the free compounds or salts, where appropriate and expedient, optionally also the salts or free compounds, respectively.

The compounds, including their salts, may also be obtained in the form of hydrates, or their crystals may, for example, include the solvent used for crystallisation.

Mixtures of isomers that are obtainable according to the invention can be separated into the individual isomers in a manner known per se: racemates, for example, by forming salts with optically pure salt-forming reagents and separating the diastereoisomeric mixture obtainable in that manner, for example by means of fractional crystallisation.

The reactions mentioned above can be carried out under reaction conditions that are known per se, in the absence or, usually, in the presence of solvents or diluents, preferably those that are inert towards the reactants used and are solvents thereof, in the absence or presence of catalysts, condensing agents or neutralising agents, and, depending on the nature of the reaction and/or of tee reactants, at reduced, normal or elevated temperature, for example in a temperature range of from approximately −70° C. to approximately 190° C., preferably from approximately −20° C. to approximately 150° C., for example at the boiling point of the solvent used, under atmospheric pressure or in a closed vessel, optionally under pressure, and/or in an inert atmosphere, for example under a nitrogen atmosphere.

The starting materials used in the process of this invention are preferably those that result in the compounds described at the beginning as being especially valuable.

The invention also relates to those embodiments of the process in which a compound obtainable as intermediate at any stage of the process is used as starting material and the remaining process steps are carried out, or in which a starting material is formed under the reaction conditions or is used in the form of a derivative, for example a salt thereof.

The present invention also relates to pharmaceutical preparations that contain one of the pharmacologically active compounds of formula I as active ingredient. Preparations for enteral, especially oral, administration and also parenteral administration are especially preferred. The preparations contain the active ingredient on its own or, preferably, together with a pharmaceutically acceptable carrier. The dosage of active ingredient depends on the disease to be treated and on the species, its age, weight and individual condition, and also on the mode of administration.

The pharmaceutical preparations contain from approximately 5% to approximately 95% active ingredient, forms of administration that are in single dose form preferably containing from approximately 20% to approximately 90% active ingredient, and forms of administration that are not in single dose form preferably containing from approximately 5% to approximately 20% active ingredient. Dosage unit forms, such as dragées, tablets or capsules, contain from approximately 0.05 g to approximately 1.0 g of active ingredient.

The pharmaceutical preparations of this invention are prepared in a manner known per se, for example by means of conventional mixing, granulating, confectioning, dissolving or lyophilising processes. For example, pharmaceutical preparations for oral administration can be obtained by combining the active ingredient with one or more solid carriers, if desired granulating a resulting mixture and, if desired, processing the mixture or granulate, optionally by the addition of additional adjuvants, into tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starches, for example maize, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional adjuvants are especially flow-regulating agents and lubricants, for example silica, talc, stearic acid or salts thereof, such as magnesium or calcium stearate, and/or polyethylene glycol, or derivatives thereof.

Dragée cores can be provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatin, and also soft sealed capsules consisting of gelatin and a plasticiser, such as glycerol or sorbitol. The dry-filled capsules may contain the active ingredient in the form of a granulate, for example in admixture with fillers, such as maize starch, binders and/or glidants, such as talc or magnesium stearate, and, if desired, stabilisers. In soft capsules, the active ingredient is preferably dissolved or suspended in suitable liquid adjuvants, such as fatty oils, paraffin oil or liquid polyethylene glycols, it being possible also to add stabilisers.

Other oral forms of administration are, for example, syrups prepared in customary manner which contain the active ingredient, for example, in suspended form and in a concentration of approximately from 5% to 20%, preferably approximately 10%, or in a similar concentration that provides a suitable single dose when administered, for example, in measures of 5 or 10 ml. Also suitable are, for example, powdered or liquid concentrates for preparing shakes, for example in milk. Such concentrates may also be packed in single dose quantities.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols.

For parenteral administration there are suitable, especially, aqueous solutions of an active ingredient in water-soluble form, for example in the form of a water-soluble salt, or aqueous injection suspensions that contain viscosity-increasing substances, for example sodium carboxymethylcellulose, sorbitol and/or dextran and, if desired, stabilisers. In addition, the active ingredient, with or without adjuvants, can also be in lyophilised form and brought into solution prior to parenteral administration by the addition of suitable solvents.

The solutions used, for example, for parenteral administration can also be used as infusion solutions.

The invention further relates to a method of treating the pathological conditions mentioned above. The compounds of this invention can be administered prophylactically or therapeutically, and are preferably administered in the form of pharmaceutical preparations. A daily dose of from approximately 0.1 g to approximately 10 g, preferably from approximately 0.5 g to approximately 5 g, of a compound of this invention will be administered in the case of a body weight of about 70 kg.

The following Examples illustrate the present invention; temperatures are given in degrees Celsius.

Example 1: 3-formylbenzamidine-2'-amidinohydrazone dihydrochloride

Crude 3-formylbenzamidine hydrochloride is dissolved in 200 ml of 96% ethanol and the solution is added to a mixture of 12.3 g (0.1 mol) of aminoguanidine sulfate, 60 ml of water and a few drops of concentrated sulfuric acid, and the whole is boiled under reflux for 15 minutes. Upon cooling, 20 g of product crystallise out in the form of the sulfate. This is added to a solution of 6.3 g (0.15 mol) of NaOH in 400 ml of ethanol and heated at 70° for 2.5 hours. After cooling, undissolved material is removed by filtration and the filtrate is concentrated by evaporation. The residue is dissolved in a small amount of ethanol and acidified with 10% ethanolic hydrochloric acid. After filtration through kieselguhr (Hyflo Super Cel ®, Fluka), concentration in vacuo is carried out until crystallisation commences. In this manner, the title compound of m.p. 206°–207° is obtained.

The starting compounds are prepared as follows:

(a) Ethyl-3-formylbenzimidate hydrochloride 59.7 ml (1.025 mol) of absolute ethanol are added to a solution of 86.7 g (0.662 mol) of 3-formylbenzonitrile in 530 ml of absolute ether and the whole is cooled to 0°. The reaction solution is saturated with dry hydrochloric acid gas and then left to stand for six days at 0°. After filtering off a fine precipitate, 1 liter of ether is added to the reaction solution, whereupon the title compound crystallises out; m.p. 126°–128° (with foaming).

(b) 3-formylbenzamidine hydrochloride 250 ml of absolute ethanol and 250 ml of saturated ethanolic ammonia solution are added to 21.3 g (0.1 mol) of the imino ether obtained in Example 1a and the whole is heated at 70° for 3 hours. After cooling, the ethanol is removed by evaporation and the residue, which corresponds to the title compound in crude form, is further reacted.

Example 2: 3-formylbenzamide-2'-amidinohydrazone hemisulfate

A solution of 4.05 g (0.033 mol) of aminoguanidine sulfate in 20 ml of water is added to a solution of 5.0 g (0.033 mol) of 3-formylbenzamide in 70 ml of ethanol. After the addition of 3 drops of concentrated sulfuric acid, the reaction mixture is boiled under reflux for 2 hours. Upon cooling, the product crystallises out. It is filtered off, boiled with ethanol, cooled, filtered again

Example 3: 3-acetylbenzamidine-2'-amidinohydrazone dihydrochloride 11.4 g (0.05 mol) of the imino ether obtained in Example 3a, 200 ml of ethanol and 125 ml of saturated ethanolic ammonia solution are boiled under reflux for 6 hours. After cooling, the reaction mixture is concentrated by evaporation, and the residue is dissolved in 4N hydrochloric acid, washed with ether and concentrated to dryness by evaporation. The resulting crude 3-acetylbenzamidine hydrochloride is dissolved in 75 ml of methanol, and a solution of aminoguanidine hydrochloride [prepared from 7.5 g (0.055 mol) of aminoguanidine hydrogen carbonate in 40 ml of water and 54 ml of 2N hydrochloric acid] is added thereto. This mixture is then heated at 70° for 1.5 hours and subsequently concentrated by evaporation. The residue is recrystallised from ethanol to yield the title compound; m.p. 185°.

The starting compounds are prepared as follows:

(a) Ethyl-3-acetylbenzimidate hydrochloride

A solution of 7.25 g (0.05 mol) of 3-acetylbenzonitrile in 150 ml of ether and 4.5 ml of ethanol is saturated at 0° with dry hydrochloric acid gas and then left to stand at 0° for 2 days. The product which crystallises out is filtered off and recrystallised from ethanol/ether; m.p. 110° (with decomposition).

Example 4: 1-hydroxy-3-(3'-amidinobenzylidene-amino)-guanidine dihydrochloride (≠3-formylbenzamidine-2'-(N-hydroxyamidino)-hydrazone dihydrochloride)

A solution of 7.3 g (0.028 mol) of 1-amino-3-hydroxyguanidine toluenesulfonate in 14 ml of water and 14.5 ml of 2N hydrochloric acid is added to a solution of 6.9 g (0.028 mol) of crude 3-formylbenzamidine hydrochloride (prepared as described in Example 1b) in 28 ml of methanol, and the reaction mixture is heated at 70° for 1 hour. It is then cooled and concentrated by evaporation, and the crude product is recrystallised from water/ethanol; m.p. 248°–250°.

Example 5: N,N'-dimethylamidinobenzaldehyde-2'-amidinohydrazone dihydrochloride A solution of 8.11 g (~0.05 mol) of N,N'-dimethylamidinobenzaldehyde in 80 ml of methanol is added dropwise to a solution of 6.71 g (0.049 mol) of aminoguanidine hydrogen carbonate in 37 ml of water and 53.4 ml of 2N hydrochloric acid. The reaction mixture is boiled under reflux for 30 minutes and then left to stand at room temperature for 24 hours. After concentration by evaporation, the crude product is purified by chromatography over Amberlite ® XAD 1180 (water as eluant) and finally recrystallised from 2N hydrochloric acid/ethanol; m.p. 103°–105°.

The starting compounds are prepared as follows:

(a) N,N'-dimethylamidinobenzaldehyde 10.7 g (0.05 mol) of the imino ether obtained in Example 1a are suspended in 125 ml of absolute ethanol, and 125 ml of a 33% solution of methylamine in ethanol (manufacturer: Fluka) are slowly added thereto. After 3 hours at 70°, the clear, pale brown reaction mixture is concentrated by evaporation, dissolved in 50 ml of 2N hydrochloric acid and washed with ether. The aqueous phase is concentrated by evaporation and the residue, which corresponds to the title compound in crude form, is further processed direct.

Example 6: 3-formylbenzamidine-thiosemicarbazone hydrochloride

A solution of 1.84 g (~0.01 mol) of crude 3-formylbenzamidine hydrochloride (prepared analogously to Example 1b) in 10 ml of methanol is added dropwise to a solution of 0.91 g (0.01 mol) of thiosemicarbazide in 5 ml of water and 10 ml of 2N hydrochloric acid. This mixture is heated under reflux for 1 hour, cooled, filtered and concentrated to dryness by evaporation. The residue is recrystallised from methanol; m.p. 210° (with decomposition). The product contains 0.5 mol of water.

Example 7: 3-formyl-N,N-dimethylbenzamidine-2'-amidinohydrazone dihydrochloride hydrate A solution of 11.7 g (~0.05 mol) of crude 3-formyl-N,N-dimethylbenzamidine hydrochloride in 50 ml of methanol is added dropwise to a solution of 6.6 g (0.049 mol) of aminoguanidine hydrogen carbonate in 35 ml of water and 51 ml of 2N hydrochloric acid. The reaction mixture is heated under reflux for 30 minutes and then concentrated by evaporation. The residue is chromatographed over Amberlite ® XAD 1180 (with water as eluant). Lyophilised product—"m.p." 80°–82°.

The starting compounds are prepared as follows:

(a) 3-Formyl-N,N-dimethylbenzamidine hydrochloride 10.7 g (0.05 mol) of the imino ether obtained in Example 1a are suspended in 125 ml of absolute ethanol, and 125 ml of a 33% dimethylamine solution in ethanol are added dropwise thereto. After a reaction period of 3 hours at 70°, the reaction mixture is concentrated by evaporation, and the residue is dissolved in 50 ml of 2N hydrochloric acid, washed with ether and again concentrated to dryness by evaporation. The resulting oil, which corresponds to the title compound in crude form, is further reacted without being purified.

Example 8: 2-amidino-6-formylpyridine-2'-amidinohydrazone dihydrochloride and 2-carbamoyl-6-formylpyridine-2'-amidinohydrazone dihydrochloride 12.5 g (0.09 mol) of aminoguanidine hydrogen carbonate are dissolved in 75 ml of water and 100 ml of 2N hydrochloric acid and, at room temperature, a solution of 33 g (~0.1 mol) of crude 2-amidino-6-formylpyridine hydrochloride in 100 ml of methanol is added thereto. The reaction mixture is heated under reflux for 1.5 hours, cooled and concentrated by evaporation. The residue is dissolved in a small amount of hot 90% ethanol and cooled slowly, whereupon 2-carbamoyl-6-formylpyridine-2'-amidinohydrazone dihydrochloride, m.p. 190°, crystallises out. It is filtered off, the mother liquor is concentrated by evaporation and the residue is chromatographed over Amberlite ® XAD 1180 (water as eluant). 2-Amidino-6-formylpyridine-2'-amidinohydrazone dihydrochloride which is obtained as the main product is finally recrystallised from ethanol: m.p. 160°.

The starting compounds are prepared as follows:

(a) 2-Amidino-6-formylpyridine hydrochloride

2-Cyano-6-formylpyridine (16.5 g ≠0.125 mol) is dissolved in 150 ml of dry ether and 150 ml of absolute ethanol, and the solution is saturated at 0° with dry hydrochloric acid gas and left to stand at 0° for 44 hours. The reddish brown reaction solution is concentrated to dryness. In order to remove excess hydrochloric acid, the residue is re-dissolved in absolute ethanol, concentrated by evaporation again and finally dried under a high vacuum. The resulting crude imino ether is dissolved in 100 ml of absolute ethanol, and a saturated ethanolic ammonia solution (100 ml) is added thereto. The reaction mixture is heated under reflux for 3 hours, cooled, filtered until clear and the filtrate is concentrated by evaporation. The solution of the residue in 100 ml of 2N hydrochloric acid is washed with ether, concentrated to dryness by evaporation and dried under a high vacuum. The title compound is obtained in crude form which is further processed direct.

Example 9:
2-amidino-4-formylpyridine-2′-amidinohydrazone dihydrochloride 11.2 g (0.08 mol) of aminoguanidine hydrogen carbonate are dissolved in 90 ml of water and 104 ml of 2N hydrochloric acid, and a solution of 52 g (~0.11 mol) of crude 2-amidino-4-formylpyridine-diethylacetal hydrochloride in 180 ml of ethanol is added thereto. The resulting mixture is heated under reflux for 1.5 hours, cooled and concentrated by evaporation. The residue is chromatographed over Amberlite ® XAD 1180 using water as eluant. The fractions that, according to thin-layer chromatography, contain the desired product are concentrated by evaporation and the residue is recrystallised from ethanol/ether; m.p. 290° (with decomposition).

The starting compounds are prepared as follows:

(a) Ethyl-4-formyl-2-pyridyl-imidate-diethylacetal hydrochloride 27 g (0.125 mol) of 2-cyano-4-formylpyridine- diethylacetal are dissolved in 250 ml of dry ether and 11.25 ml of absolute ethanol. This solution is saturated at 0° with dry hydrochloric acid gas (about 50 g) and stirred for 1 hour at 0°. The product which precipitates is filtered off, washed with cold ether and dried: m.p. 95°–97°.

(b) 2-Amidino-4-formylpyridine-diethylacetal hydrochloride 37.0 g (0.128 mol) of the imino ether obtained in Example 9a are dissolved in 277 ml of absolute ethanol and, at room temperature, 470 ml of a saturated ethanolic ammonia solution are added thereto. After 2 hours at 70° (reflux), the reaction mixture is cooled and concentrated by evaporation, and the residue is dissolved in 2N hydrochloric acid, washed with ether and, finally, again concentrated to dryness by evaporation. The crude product, which is still slightly moist, is further processed without being further purified.

Example 10:
3-amino-1-(3′-amidinobenzylidene-amino)-guanidine dihydrochloride and 1,3-bis(3′-amidinobenzylidene-amino)-guanidine trihydrochloride 1.25 g (0.01 mol) of 1,3-diaminoguanidine hydrochloride are dissolved in 10 ml of water and, at room temperature, a solution of 1.84 g (~0.01 mol) of crude 3-formylbenzamidine hydrochloride (Example 1b) in 10 ml of methanol is added thereto. The mixture is stirred at room temperature for 16 hours and then concentrated by evaporation. The residue is taken up in ethanol, freed of undissolved material by filtration and again concentrated by evaporation. The resulting oil is chromatographed over Amberlite ® XAD 1180 with water. Fractions 10–13 correspond to 3-amino-1-(3′-amidinobenzylidene-amino)-guanidine dihydrochloride (decomposition at 160°) and fractions 15–20 correspond to 1,3-bis(3′-amidinobenzylidene-amino)-guanidine trihydrochloride dihydrate (decomposition at 180°).

Example 11:
3-formyl-N-n-butylbenzamidine-2′-amidinohydrazone dihydrochloride 1.22 g (0.0099 mol) of aminoguanidine hydrogen carbonate are dissolved in 10 ml of water and 10 ml of 2N hydrochloric acid and, at room temperature, a solution of about 2.4 g (~0.01 mol) of crude 3-formyl-N-n-butyl-benzamidine hydrochloride in 15 ml of ethanol is added thereto. The mixture is cooled, concentrated to dryness by evaporation and chromatographed over a column of Amberlite ® XAD 1180 (water as eluant). Recrystallisation from ethanol/ether yields the title compound, m.p. 230°.

The starting compounds are prepared as follows:

(a) 3-Formyl-N-n-butylbenzamidine hydrochloride

With stirring at room temperature, 2.0 ml (0.02 mol) of n-butylamine are added to 2.1 g (0.01 mol) of ethyl-3-formylbenzimidate hydrochloride (Example 1a) in 15 ml of absolute ethanol. The reaction mixture is heated under reflux for 3 hours, cooled and further reacted direct.

Example 12:
3-formylbenzamidine-2′-(N-n-butylamidino)-hydrazone dihydrochloride A solution of 1.66 g (0.01 mol) of 1-amino-3-n-butyl-guanidine hydrochloride in 30 ml of 50% ethanol is added at room temperature to a solution of about 1.8 g (0.01 mol) of 3-formylbenzamidine hydrochloride (Example 1b) and the whole is heated at about 70° (reflux) for 2 hours. The clear reaction solution is cooled and concentrated by evaporation, and the residue is chromatographed over a column of Amberlite ® XAD 1180 (water as eluant). Fractions 14–30 yield, after recrystallisation from ethanol/ether, the title compound with a decomposition point of 140°.

Example 13:
N-(3acetylphenyl-2′-amidinohydrazone)-guanidine dihydrochloride 15.4 g of cyanamide (H₂N—CN) are added to a suspension of 14.0 g of 3-aminoacetophenone-2′-amidinohydrazone hydrochloride in 360 ml of ethanol and 102.8 ml of 0.6N ethanolic hydrochloric acid and the reaction mixture is boiled under reflux for 65 hours.

It is filtered while hot, and the crystals obtained are then washed with a small amount of ethanol and subsequently dried in vacuo at 40°. In this manner, the title compound is obtained. M.p. >250°.

Example 14:
3-formyl-N-n-butylbenzamidine-2'-(N-n-butylamidino)-hydrazone dihydrochloride 1.7 g (0.01 mol) of 1-amino-3-n-butylguanidine hydrochloride are dissolved in 30 ml of 50% ethanol, and a solution of about 2.4 g (0.01 mol) of crude 3-formyl-N-n-butylbenzamidine hydrochloride (Example 11a) in 20 ml of ethanol are added thereto. The reaction mixture is subsequently heated under reflux for 1 hour, cooled, concentrated by evaporation and chromatographed over Amberlite® XAD 1180 (water as eluant). The fractions containing the product are concentrated by evaporation and the residue is recrystallised from ethanol/ether with the addition of ethanolic hydrochloric acid. Crystals that are very hygroscopic are obtained; 1H-NMR: $\delta$=0.8-1.0 (m, 6H); 1.20-1.75 (m, 8H); 3.46 (q, J=6 Hz, 4H). MS: m/e 317 (M+1), 316 (M+), 244, 202, 176 (100%).

Example 15:
N-(3-acetylphenyl-2'-amidinohydrazone)-guanidine dihydrochloride A solution of 1.59 g of 3-guanidinoacetophenone [J. Med. Chem. 10, 1123 (1967)] in 10 ml of methanol is added to a solution of 1.36 g of aminoguanidine hydrogen carbonate in 5 ml of 4.0N hydrochloric acid and the reaction mixture is boiled under reflux for 22 hours. It is then concentrated to dryness by evaporation and the residue is recrystallised from 50 ml of ethanol. In this manner, the title compound is obtained. M.p. >250°.

Example 16:
N-(3-guanidinobenzylideneamino)-guanidine dihydrochloride 1.5 g of cyanamide and 12.5 ml of 0.95N ethanolic hydrochloric acid are added to a solution of 2.5 g (10 mmol) of 3-aminobenzylideneamino-guanidine dihydrochloride [see Chem. Abstr. 57, 9826a (1957)] in 90 ml of absolute ethanol, and the reaction mixture is boiled under reflux for 89 hours. It is then cooled and concentrated to half. The product which crystallises out is filtered off with suction, washed with a small amount of ethanol and dried. In this manner, the title compound is obtained. M.p. >250°.

Example 17:
4-amidino-2-formylpyrimidine-2'-amidinohydrazone dihydrochloride 100 mg (0.41 mmol) of 4-cyano-2-formylpyrimidine-2'-amidinohydrazone hydrochloride are dissolved in 2 ml of absolute methanol; 100 mg of molecular sieve 3 Å are added thereto and the whole is stirred at room temperature under argon for 1 hour. 91 µl of an approximately 5.4M solution of sodium methanolate in methanol is then added thereto and stirring is continued for 2 hours at 50° and then for a further 3 hours at room temperature. When conversion to the imino ester is complete (monitored by HPLC), 24.1 mg of ammonium chloride (dry) are added to the reaction mixture which is then stirred at room temperature for 21 hours. After the addition of a second portion of ammonium chloride (11 mg), the reaction mixture is stirred for 3 hours at 50° and filtered with suction over Hyflo Super Cel® (kieselguhr), and the solvent is distilled off in vacuo. The residue is dissolved in a small amount of water and, at 0°, 1.64 ml of 0.1N hydrochloric acid are added thereto. "Reverse phase" chromatography on Opti-UP-$C_{12}$ silica gel (Antecgel-dodecyltrichlorosilane, produced by Antec) in water yields, after evaporation of the water, the title compound; 1H-NMR (DMSO-$d_6$): $\delta$=9.30 (d, 1H); 8.46 (d, 1H); 8.35 (s, 1H).

The starting compound is prepared as follows:

(a)
6-Hydroxy-4-methyl-2-(2-phenylethenyl)-pyrimidine [see Chem. Pharm. Bull. 13, 1183 (1965)]

48.8 ml of freshly distilled benzaldehyde are added to 60 g (0.483 mol) of 6-hydroxy-2,4-dimethylpyridimine [see Tetrahedron 35, 2087 (1979)] in 180 ml of acetic anhydride and the whole is heated under argon at 130° for 23 hours. When cool, the reaction mixture is poured into 2 liters of ice-cold ether, the batch is stirred for 1 hour while cooling with ice and the resulting precipitate is filtered off with suction. The yellow-brown crystals are washed with ether and recrystallised from methanol; m.p. 217°-219°.

(b) 6-Chloro-4-methyl-2-(2-phenylethenyl)-pyrimidine 212 mg (1 mmol) of 6-hydroxy-4-methyl-2-(2-phenylethenyl)-pyrimidine in 1 ml of phosphorus oxychloride are boiled under reflux for 35 minutes under nitrogen. When cool, the reaction mixture is poured onto ice, and the aqueous solution is neutralised with sodium hydroxide solution and extracted several times with ether. The ether extracts are washed with water and saturated sodium chloride solution, dried over $CaCl_2$, filtered with suction and concentrated. Purification is effected by sublimation in a bulb tube oven at 150° oven temperature and in vacuo (0.1 mm Hg $\neq$0.13 mbar). Colourless crystals of m.p. 71°-73° are obtained.

(c) 4-Methyl-2-(2-phenylethenyl)-pyrimidine 9.02 ml of triethylamine and 1.365 g of Lindlar catalyst are added to 13.65 g (59.17 mmol) of 6-chloro-4-methyl-2-(2-phenylethenyl)pyrimidine in 220 ml of absolute ethanol and hydrogenation is carried out at room temperature under normal pressure. When 1 equivalent of hydrogen has been absorbed, hydrogenation is terminated (after about 7.5 hours), and the reaction mixture is filtered with suction over Hyflo Super Cel® and concentrated in a rotary evaporator. Chromatography twice on silica gel with chloroform and then n-hexane/ethyl acetate 5-20% as eluants yields the pure title compound; m.p. 65°-67°.

(d)
4-N-hydroxyiminomethyl-2-(2-phenylethenyl)-pyrimidine 416 ml of liquid ammonia are introduced under nitrogen into a 4-necked flask cooled with acetone/dry ice and equipped with a magnetic stirrer, gas inlet pipe, thermometer, and a cooling member filled with dry ice. To this there are added, under nitrogen and with stirring, 2.91 g (126.7 mmol) of metallic sodium cut into small pieces, followed by 100 mg of iron(III) chloride (anhydrous). The mixture is allowed to boil under reflux for 20 minutes (cooling bath −20°). A blackish blue solution is obtained to which there are added over a period of 10 minutes 8.16 g (41.16 mmol) of pulverised 4-methyl-2-(2-phenylethenyl)-pyrimidine (in 3 portions). The reaction mixture is allowed to boil under reflux for a further 60 minutes and then 9.7 ml (2 equivalents) of n-butyl nitrite are added dropwise thereto over a period of 10 minutes. A red solution is obtained which is allowed to boil under reflux for a further 60 minutes. 6.93 g (129 mmol) of ammonium chloride are then added (in portions) to the reaction mixture, the cooling bath is removed and the ammonia is allowed to evaporate off at room temperature. The solid grey residue is boiled up with acetone, filtered off and the solution is concentrated. The crude product is purified by chromatography on silica gel, eluant methylene chloride/acetone 5-10%. The resulting title compound is a syn-anti-mixture of the two oximes. $^1$H-NMR (DMSO-d$_6$): δ=12.65 and 12.29 (bs, 1H); 8.94/d and 8.80/d (1H); 8.15/d and 7.61/d (1H); 8.09/s and 7.57/s (1H); 7.97/d and 7.96/d (1H); 7.31/d and 7.29/d (1H).

(e) 4-Cyano-2-(2-phenylethenyl)-pyrimidine 425 mg (1.88 mmol) of 4-N-hydroxyiminomethyl-2-(2-phenylethenyl)pyrimidine (syn-anti-mixture) in 4.25 ml of POCl$_3$ are heated at 120° under nitrogen for 1 hour. When cooled to about 70°, the solution is poured onto a mixture consisting of 50 g of ice and 22 ml of 28% aqueous ammonia solution, is saturated with solid K$_2$CO$_3$ and extracted three times with ethyl acetate. The organic phase is washed neutral, dried over Na$_2$SO$_4$ and concentrated. For purification, the concentrate is recrystallised from chloroform/ether; m.p. 147°-150° (colourless crystals).

(f) 4-Cyano-2-formylpyrimidine 2.238 g (10.81 mmol) of 4-cyano-2-(2-phenylethenyl)-pyrimidine in 150 ml of absolute methanol and 75 ml of absolute methylene chloride are cooled to −70° C. Ozone is passed through until a blue solution is produced (about 0.5 hour). Nitrogen is passed through the solution until the excess ozone has been removed (about 0.75 hour) and then 3.5 ml of dimethyl sulfide are added to the reaction mixture. The solution is allowed to warm up to room temperature and is concentrated in a rotary evaporator. The crude product is purified over silica gel (eluant: n-hexane/ethyl acetate 1:3). 1H-NMR (CDCl3): δ=10.11 (s, 1H); 9.23 (d, 1H); 7.82 (d, 1H).

(g) 4-Cyano-2-formylpyrimidine-2'-amidinohydrazone hydrochloride 1.65 ml of 2N HCl are added to 207 mg (1.49 mmol) of aminoguanidine hydrogen carbonate in 1.14 ml of water, followed by the addition of 200 mg (1.5 mmol) of 4-cyano-2-formylpyrimidine and 1.5 ml of methanol. The reaction mixture is heated to 70°, a clear solution being formed. After 45 minutes at that temperature, the reaction mixture is extensively concentrated and the resulting precipitate is filtered off with suction. It is washed with a small amount of cold water and cold ethanol and the title compound is dried at 40° under a high vacuum. 1H-NMR (DMSO-d$_6$): δ=12.65/bs and 7.97/bs (NH; replaced by D$_2$O), 9.23 (d, 1H); 8.30 (s, 1H); 8.16 (s, 1H).

Example 18:
4-(N-methylamidino)-2-formylpyrimidine-2'-amidinohydrazone dihydrochloride Starting from 4-cyano-2-formylpyrimidine-2'-amidinohydrazone hydrochloride (Example 17g) and methylamine hydrochloride, the title compound is obtained in a manner analogous to that of Example 17; $^1$H-NMR (DMSO-d$_6$): δ=9.30 (d, 1H); 8.62 (d, 1H); 8.38 (s, 1H); 3.15 (d, 1H).

Example 19:
4-(N-ethylamidino)-2-formylpyrimidine-2'-amidinohydrazone dihydrochloride 200 mg (0.819 mmol) of 2-cyano-2-formylpyrimidine-2'-amidinohydrazone hydrochloride (Example 17g) are introduced under argon into 8 ml of absolute methanol, and 0.3 ml of a 5.4M methanolic sodium methanolate solution is added thereto. After stirring for 6 hours at 50°, the reaction mixture is cooled to room temperature and 86.9 mg (1.06 mmol) of ethylamine hydrochloride are added thereto. The reaction mixture is stirred overnight at room temperature, a further 20 mg (0.24 mmol) of ethylamine hydrochloride are added and stirring is continued at room temperature for 22 hours. It is then heated at 50° for a further hour, the solution is cooled and the mixture is extensively concentrated. The residue is taken up in water and adjusted to about pH 1.5 by the addition of 1N hydrochloric acid at 0°. Purification of the title compound is effected by chromatography on Opti-Up silica gel. $^1$H-NMR (DMSO-d$_6$): δ=9.30 (d, 1H); 8.49 (d, 1H); 8.36 (s, 1H); 3.57 (m, 2H); 1.24 (t, 3H).

Example 20:
4-(N-n-propylamidino)-2-formylpyrimidine-2'-amidinohydrazone dihydrochloride Analogously to Example 19, the title compound is obtained from 4-cyano-2-formylpyrimidine-2'-amidinohydrazone hydrochloride (Example 17g) after treatment with sodium methanolate and n-propylamine hydrochloride. $^1$H-NMR (DMSO-d$_6$): δ=9.29 (d, 1H); 8.49 (d, 2H); 8.37 (s, 1H); 3.53 (m, 2H); 1.68 (m, 2H); 0.93 (t, 3H).

Example 21:
4-(N-hydroxyamidino)-2-formylpyrimidine-2'-amidinohydrazone hydrochloride Analogously to Example 19, the title compound is obtained from 4-cyano-2-formylpyrimidine-2'-amidinohydrazone hydrochloride (Example 17g) after treatment with sodium methanolate and hydroxylamine hydrochloride. $^1$H-NMR (DMSO-d$_6$): δ=12.67 (s, OH); 8.85 (d, 1H); 8.26 (s, 1H); 7.82 (d, 1H).

Example 22:
1-hydroxy-3-(2'-amidino-6'-pyridylmethylidene-amino)-guanidine di-p-toluenesulfonate A solution of 1.99 g (0.0076 mol) of 1-amino-3-hydroxyguanidine toluene-sulfonate in 4 ml of water is added to a solution of 2.2 g (0.0076 mol) of 2-amidino-6-formylpyridine-diethylacetal hydrochloride (Example 9b) in 15 ml of methanol and, after the addition of 3.7 ml of 2N hydrochloric acid, the reaction mixture is heated at 70° for 1 hour. After cooling, it is concentrated by evaporation and the residue is taken up in a small amount of ethanol, the undissolved material is filtered off and the residue is again concentrated by evaporation. The crude product is purified by chromatography over Amberlite® XAD 1180 (water as eluant) and subsequently recrystallised from ethanol/ether; m.p. 230°-235° (with decomposition).

Example 23:
2-(N-methoxyamidino)-6-formylpyridine-2'-amidinohydrazone dihydrochloride 0.85 g (0.0038 mol) of 2-cyano-6-formylpyridine-2'-amidinohydrazone hydrochloride is added at room temperature to a solution of 0.17 g (0.0076 g-atom) of sodium in 6 ml of absolute methanol, and the reddish suspension is stirred at room temperature for 12 hours. To the imino ether formed therefrom in situ there is added 0.63 g (0.0076 mol) of O-methylhydroxylamine hydrochloride and the reaction mixture is then stirred at room temperature for a further 12 hours and subsequently filtered. The filtrate is concentrated by evaporation and the residue is taken up in a small amount of ethanol and filtered again. After the addition of ethanolic hydrochloric acid, the title compound crystallises out; m.p. 230°-234°.

The starting compound is prepared as follows:

(a) 2-Cyano-6-formylpyridine-2'-amidinohydrazone hydrochloride 22 ml of 2N hydrochloric acid are added dropwise to a solution of 3.09 g (0.022 mol) of aminoguanidine hydrogen carbonate in 15 ml of water ($CO_2$ evolution). To this solution are added 3.0 g (0.022 mol) of 2-cyano-6formylpyridine dissolved in 15 ml of methanol and the reaction mixture is heated at 70° for 1 hour. After cooling, the title compound is filtered off, washed with a small amount of methanol/water (1:1) and dried: m.p. 295°-298°.

Example 24:
2-(N-aminoamidino)-6-formylpyridine-2'-amidinohydrazone dihydrochloride Analogously to Example 23, the imino ether formed as intermediate is reacted with hydrazine dihydrochloride to give the title compound; m.p. 245°-248°.

Example 25:
2-(4',5'-dihydroimidazol-2'-yl)-6-formylpyridine-2''-amidinohydrazone dihydrochloride Analogously to Example 23, the imino ether formed as intermediate is reacted with 1,2-diaminoethane dihydrochloride to give the title compound; m.p. 310°-313°.

Example 26:
2-(N-hydroxyamidino)-6-formylpyridine-2'-amidinohydrazone tetrahydrochloride Analogously to Example 23, the imino ether formed as intermediate is reacted with hydroxylamine hydrochloride to give the title compound; m.p. 260°-263° (the product contains 3 mol of water).

Example 27:
1-amino-3-(2'-amidino-6'-pyridylmethylidene-amino)-guanidine dihydrochloride Analogously to Example 22, 2-amidino-6-formylpyridine- diethylacetal hydrochloride (Example 9b) is reacted with a five-fold excess of 1,3-diaminoguanidine hydrochloride to give the title compound; m.p. 250°-253°.

Example 28:
1,3-bis(2'-amidino-6'-pyridylmethylidene-amino)-guanidine trihydrochloride Analogously to Example 22, 2-amidino-6-formylpyridine-diethylacetal hydrochloride (Example 9b) is reacted with 0.5 equivalent of 1,3-diaminoguanidine hydrochloride to give the title compound; m.p. 260°-265°.

Example 29:
N-(3-propionylphenyl-2'-amidinohydrazone)-guanidine dihydrochloride Using 3-aminopropiophenone and aminoguanidine hydrogen carbonate as starting materials, the title compound is obtained analogously to Example 13 via 3-aminopropiophenone-2'-amidinohydrazone hydrochloride.

Example 29a:
N-(3-propionylphenyl-2'-amidinohydrazone)-guanidine dihydrochloride Analogously to Example 15, the title compound is prepared using 3-guanidinopropiophenone and aminoguanidine hydrogen carbonate as starting materials.

Example 30:
N-(3-isobutyroylphenyl-2'-amidinohydrazone)-guanidine dihydrochloride Using 3-aminoisobutyrophenone and aminoguanidine hydrogen carbonate as starting materials, the title compound is obtained analogously to Example 13 via 3-aminoisobutyrophenone-2'-amidinohydrazone hydrochloride.

Example 30a:
N-(3-isobutyroylphenyl-2'-amidinohydrazone)-guanidine dihydroehloride Analogously to Example 15, the title compound is prepared using 3-guanidinoisobutyrophenone and aminoguanidine hydrogen carbonate as starting materials.

Example 31:
2-amidino-6-acetylpyridine-2'-amidinohydrazone dihydrochloride

Analogously to Example 8a and 8, the title compound is prepared using 2-cyano-6-acetylpyridine as starting material.

Example 32:
2-amidino-6-propionylpyridine-2'-amidinohydrazone dihydrochloride Analogously to Example 8a and 8, the title compound is prepared using 2-cyano-6-propionylpyridine as starting material.

Example 33:
2-amidino-6-isobutyroylpyridine-2'-amidinohydrazone dihydrochloride Analogously to Example 8a and 8, the title compound is prepared using 2-cyano-6-isobutyroylpyridine as starting material.

Example 34:
4-amidino-2-acetylpyridine-2'-amidinohydrazone dihydrochloride Analogously to Example 8a and 8, the title compound is prepared using 4-cyano-2-acetylpyridine as starting material.

Example 35:
4-amidino-2-propionylpyridine-2'-amidinohydrazone dihydrochloride Analogously to Example 8a and 8, the title compound is prepared using 4-cyano-2-propionylpyridine as starting material.

Example 36:
3-propionylbenzamidine-2'-amidinohydrazone dihydrochloride

Analogously to Example 3a and 3, the title compound is prepared using 3-propionylbenzonitrile as starting material.

Example 37:
3-isobutyroylbenzamidine-2'-amidinohydrazone dihydrochloride Analogously to Example 3a and 3, the title compound is prepared using 3-isobutyroylbenzonitrile as starting material.

Example 38:
2-amidino-4-formylpyrimidine-2'-amidinohydrazone dihydrochloride Analogously to Example 17, the title compound is obtained using 2-cyano-4-formylpyrimidine-2'-amidinohydrazone hydrochloride as starting material. The starting material is prepared from 2-cyano-4-methylpyrimidine by oxidation with selenium oxide and reaction of the resulting 2-cyano-4-formylpyrimidine with aminoguanidine hydrogen carbonate.

Example 39:
2-Amidino-4-formylpyrimidine-2'-amidinohydrazone dihydrochloride 200 mg (0.8 mmol) of 2-cyano-4-formylpyrimidine-2'-amidinohydrazone hydrochloride and 300 mg of molecular sieve 3 Å in 10 ml methanol are stirred at room temperature for 1 hour. 0.97 ml of 1.9M solution of sodium methoxide in absolute methanol is then added, and the stirring is continued for 2.5 hours at 50°. The reaction mixture is then treated with 64.1 mg of dry ammonium chloride and is stirred for further 7 hours at 50°. After cooling, 1N HCl is added until pH 2-3, the reaction mixture is filtered and evaporated. The residue is dissolved in a small amount of water and purified by "reverse phase" chromatography on Opti-UP-C$_{12}$® silica gel (Antec) with water. The title compound is then crystallized from methanol and ether; FAB (MS): (M+H)+ =207; $^1$H-NMR (DMSO-d$_6$): δ=9.6–10.0 (bm); 9.16 (d); 8.62 (d); 8.0–8.2 (bm).

The starting compounds are prepared as follows:

(a) 4-(β-styryl)-2-trimethylammonium-pyrimidine chloride 5.3 g (0.0244 mol) of 2-chloro-4-(β-styryl)pyrimidine (see Acta Chem. Scand. 43, 62–68 (1989)) is dissolved in 100 ml of 1.92M trimethylamine in benzene and stirred for 24 hours at room temperature in argon atmosphere. Then 400 ml ether is added, and after one further hour the precipitated title compound is filtered off, washed with cold ether and dried; $^1$H-NMR (DMSO-d$_6$): δ=9.02 (d); 8.18 (d); 7.89 (d); 3.65 (s).

(b) 2-Cyano-4-(β-styryl)pyrimidine 7.0 g (0.0244 mol) of 4-(β-styryl)-2-trimethylammonium-pyrimidine chloride are dissolved in 55 ml methylenechloride, and a solution of 4.433 g (0.0244 mol) of tetraethylammonium cyanide in 55 ml methylenechloride is added during 5 minutes. The reaction mixture is stirred for one hour at room temperature, and then washed with water and dilute brine, dried (Na$_2$SO$_4$) and evaporated. The title compound is purified by chromatography on silica gel (eluent: n-hexane/ethyl acetate 1:1); $^1$H-NMR (DMSO-d$_6$): δ=8.93 (d); 8.02 (d); 7.91 (d); 7.7–7.85 (m); 7.35–7.55 (m); 7.39 (d).

(c) 2-Cyano-4-formylpyrimidine

A solution of 1.211 g (0.0059 mol) of 2-cyano-4-(β-styryl)pyrimidine in 85 ml of absolute methanol and 55 ml of methylenechloride is cooled to −70°. Ozone is passed through until a blue solution is produced (about 0.5 hour). Then nitrogen is passed through the solution until the excess of ozone has been removed (15 min.), and 1.95 ml dimethyl sulfide are added to the reaction mixture. The solution is allowed to warm up to room temperature and is concentrated in a rotatory evaporator. The crude product is purified over silica gel (eluent: n-hexane/ethyl acetate 1:1); $^1$H-NMR (DMSO-d$_6$): δ=9.94 (s); 9.32 (d) 8.18 (d).

(d) 2-Cyano-4-formylpyrimidine-2'-amidinohydrazone hydrochloride 3.01 ml of 2N HCl are added to 390 mg of aminoguanidine hydrogen carbonate in 2 ml of water, followed by the addition of a solution of 382 mg (0.0029 mol) 2-cyano-4-formylpyrimidine in 4 ml methanol. The reaction mixture is heated to 70° for 2 hours, and is then extensively concentrated until the title compound crystallizes. It is filtered off with suction, washed with cold water and ether, and dried; $^1$H-NMR (DMSO-d$_6$, important signals): δ=12.74 (s); 9.08 (d); 8.64 (d).

Example 40:

Capsules, each containing 0.25 g of active ingredient, for example one of the compounds of Examples 1 to 38, can be prepared as follows:

| Composition (for 5000 capsules) | |
| --- | --- |
| active ingredient | 1250 g |
| talc | 180 g |
| wheat starch | 120 g |
| magnesium stearate | 80 g |
| lactose | 20 g |

The pulverulent substances are forced through a sieve of 0.6 mm mesh width and mixed. Portions each of 0.33 g of the mixture are introduced into gelatin capsules by means of a capsule filling machine.

What is claimed is:

1. A compound of formula I

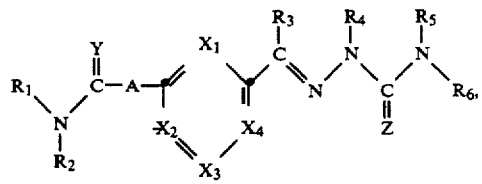

(I)

wherein A is a single bond or a group $NR_7$; each of $X_1$, $X_2$, $X_3$, and $X_4$ is CH; Y is $NR_8$ or also, if A is a single bond, is O; Z is $NR_9$, O or S; $R_1$ is hydrogen, lower alkyl, hydroxy, lower alkoxy, lower alkanoyloxy, amino, lower alkylamino, di-lower alkylamino, lower alkyleneamino, morpholino, thiomorpholino, piperazino or 4-lower alkylpiperazino; each of the radicals $R_2$, $R_3$, $R_4$, $R_5$, $R_7$, $R_8$, and $R_9$, independently of the others, is hydrogen or lower alkyl; and $R_6$ is a group

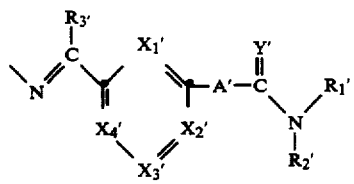

wherein A′, $X_1'$, $X_2'$, $X_3'$, $X_4'$, Y′, $R_1'$, $R_2'$ and $R_3'$ have the same definitions as the corresponding radicals A, $X_1$, $X_2$, $X_3$, $X_4$, Y, $R_1$, $R_2$ and $R_3$, a tautomer thereof, [with the exception of a compound wherein A is a single bond, each of $R_1$, $R_2$, $R_3$, $R_4$ and $R_5$ is hydrogen, Y is NH, Z is NH and each of $X_2$, $X_2$, $X_3$ and $X_4$ is CH] or a pharmaceutically acceptable salt thereof.

2. A compound of formula I according to claim 1 wherein A is a single bond or a group $NR_7$; each of $X_1$, $X_2$, $X_3$ and $X_4$ is CH; Y is $NR_8$ or also, if A is a single bond, is O; Z is $NR_9$, O or S; $R_1$ is hydrogen, lower alkyl, hydroxy, lower alkoxy or amino: each of the radicals $R_2$, $R_3$, $R_4$, $R_5$, $R_7$, $R_8$, and $R_9$, independently of the others, is hydrogen or lower alkyl; and $R_6$ is a group

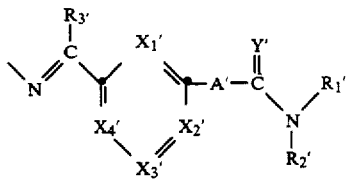

wherein A′, $X_1'$, $X_2'$, $X_3'$, $X_4'$, $R_1'$, $R_2'$ and $R_3'$ have the same definitions as the corresponding radicals A, $X_1$, $X_2$, $X_3$, $X_4$, Y, $R_1$, $R_2$ and $R_3$, a tautomer thereof, [with the exception of a compound wherein A is a single bond, each of $R_1$, $R_2$, $R_3$, $R_4$ and $R_5$ is hydrogen, Y is NH, Z is NH and each of $X_1$, $X_2$, $X_3$ and $X_4$ is CH], or a pharmaceutically acceptable salt thereof.

3. A compound of formula I according to claim 1, wherein A is a single bond or an NH group; wherein each of $X_1$, $X_2$, $X_3$ and $X_4$ is CH; Y is $NR_8$ or also, if A is a single bond, is O: Z is NH or S; $R_1$ is hydrogen, lower alkyl, hydroxy, lower alkoxy or amino: each of the radicals $R_2$, $R_3$ and $R_8$, independently of the others, is hydrogen or lower alkyl; $R_4$ and $R_5$ are hydrogen, and $R_6$ is 3-amidinophenyl-methylideneamino, a tautomer thereof, [with the exception of a compound wherein A is a single bond, each of $R_1$, $R_2$, $R_3$, $R_4$ and $R_5$ is hydrogen, Y is NH, Z is NH and each of $X_1$, $X_2$, $X_3$ and $X_4$ is CH] or a pharmaceutically acceptable salt thereof.

4. A pharmaceutical composition comprising a therapeutically effective amount of a compound according to claim 1 and at least one pharmaceutically acceptable carrier.

5. A method of treating a disease responsive to S-adenosylmethionine decarboxylase inhibition in mammals comprising the administration to a mammal in need thereof a therapeutically effective amount of the formula I according to claim 1.

* * * * *

UNITED STATES PATENT AND TRADEMARK OFFICE
CERTIFICATE OF CORRECTION

PATENT NO. : 5,376,685
DATED : December 27, 1994
INVENTOR(S) : Stanek, et al

It is certified that error appears in the above-indentified patent and that said Letters Patent is hereby corrected as shown below:

In claim 1, column 27, lines 31-33, delete "[with the exception of a compound wherein A is a single bond, each of $R_1$, $R_2$, $R_3$, $R_4$ and $R_5$ is hydrogen, Y is NH, Z is NH and each of $X_2, X_2, X_3$ and $X_4$ is CH]"

In claim 2, column 28, line 12, after "$X_4$'" insert --Y',--

In claim 2, column 28, lines 14-17, delete "[with the exception of a compound wherein A is a single bond, each of $R_1, R_2, R_3$, $R_4$ and $R_5$ is hydrogen, Y is NH, Z is NH and each of $X_1, X_2, X_3$ and $X_4$ is CH]"

In claim 3, column 28, lines 27-30, delete "[with the exception of a compound wherein A is a single bond, each of $R_1, R_2, R_3, R_4$, and $R_5$ is hydrogen, Y is NH, Z is NH and each of $X_1, X_2, X_3$ and $X_4$ is CH]"

Signed and Sealed this

Fourteenth Day of March, 1995

*Attest:*

BRUCE LEHMAN

*Attesting Officer*      *Commissioner of Patents and Trademarks*